US007417665B2

(12) United States Patent
Banju et al.

(10) Patent No.: US 7,417,665 B2
(45) Date of Patent: Aug. 26, 2008

(54) STEREOSCOPIC IMAGE OBSERVING APPARATUS

(75) Inventors: Kazuo Banju, Hachioji (JP); Masahiro Kudo, Hino (JP); Shingo Nogami, Machida (JP); Takahiro Kogasaka, Hachioji (JP); Kazuo Morita, Hachioji (JP); Masayuki Irie, Hachioji (JP)

(73) Assignee: Olympus Corporation, Tokyo (JP)

( * ) Notice: Subject to any disclaimer, the term of this patent is extended or adjusted under 35 U.S.C. 154(b) by 555 days.

(21) Appl. No.: 10/846,969

(22) Filed: May 14, 2004

(65) Prior Publication Data

US 2004/0263614 A1 Dec. 30, 2004

(30) Foreign Application Priority Data

May 16, 2003 (JP) .............................. 2003-139523

(51) Int. Cl.
*H04N 13/00* (2006.01)
*H04N 13/04* (2006.01)
*H04N 15/00* (2006.01)

(52) U.S. Cl. .............................. 348/58; 348/42; 348/51
(58) Field of Classification Search ............. 348/52–60; 600/166; 359/465–466, 475
See application file for complete search history.

(56) References Cited

U.S. PATENT DOCUMENTS

| 6,095,652 | A  | * | 8/2000 | Trayner et al. | ................. | 353/10 |
| 6,215,590 | B1 | * | 4/2001 | Okano | ......................... | 359/464 |
| 6,250,778 | B1 | * | 6/2001 | Doumuki | ..................... | 362/327 |
| 6,752,498 | B2 | * | 6/2004 | Covannon et al. | ........... | 351/240 |
| 2003/0151809 | A1 | * | 8/2003 | Takahashi et al. | ........... | 359/462 |

* cited by examiner

*Primary Examiner*—John P. Leubecker
*Assistant Examiner*—Philip R Smith
(74) *Attorney, Agent, or Firm*—Scully, Scott, Murphy & Presser, P.C.

(57) ABSTRACT

A stereoscopic image observing apparatus includes a right-eye projector 1 and a left-eye projector 2 which illuminate projected light for right and left eyes with the parallax generated based on an image pick-up signal obtained from a stereoscopic endoscope 8, a Fresnel lens 17 which applies and reflects the lens operation with the positive polarity to the projected light of the illuminated images for the right and left eyes, and an optical shift element layer 16 having liquid crystal 20 and a double refraction plate 19 for changing and diffusing on time series the reflecting position of the reflected light of the images for the right and left eyes from the Fresnel lens 17.

3 Claims, 13 Drawing Sheets

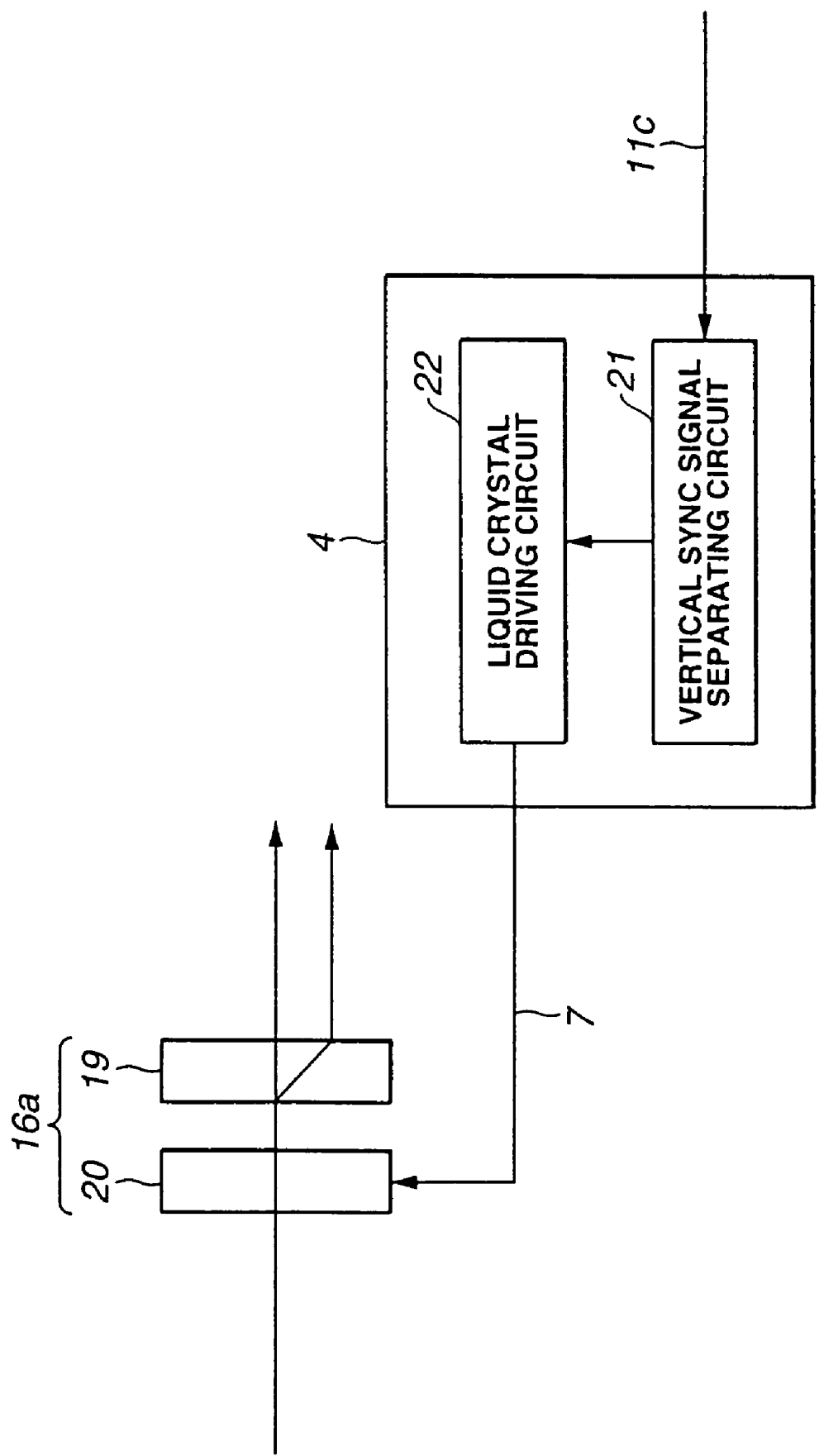

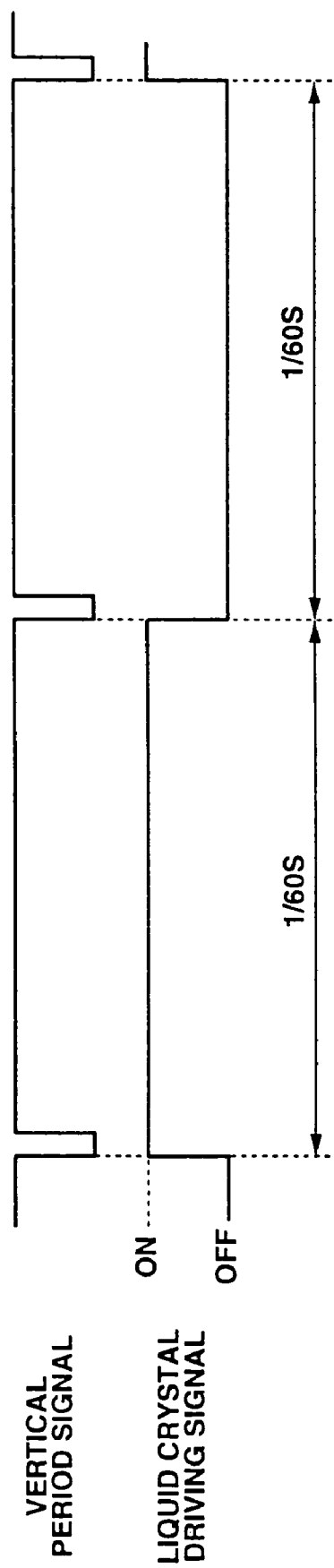

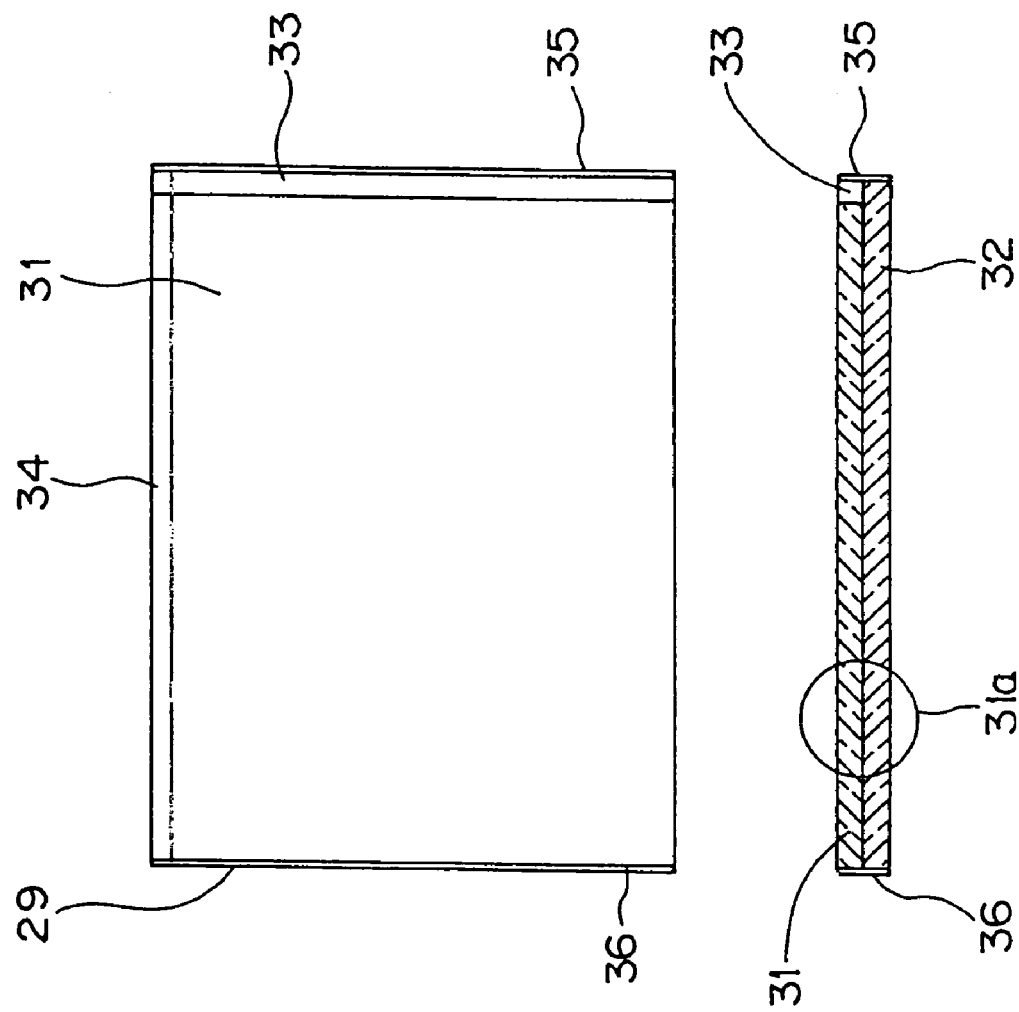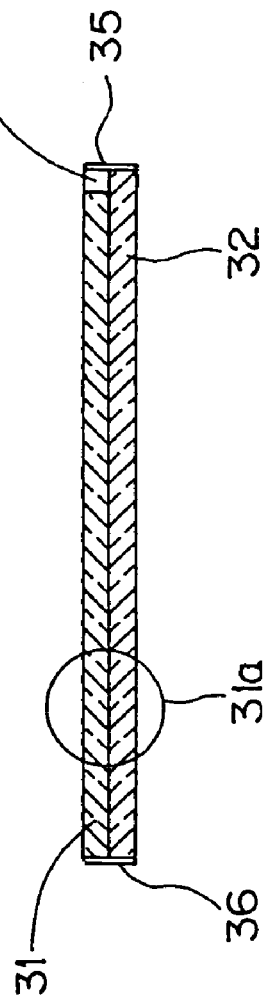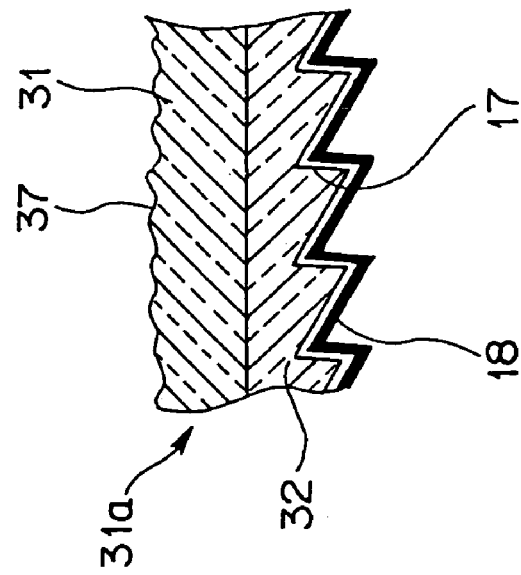

STEREOSCOPIC IMAGE OBSERVING APPARATUS

This application claims benefits of Japanese Patent Application No. 2003-139523 filed in Japan on May 16, 2003, the contents of which are incorporated by this reference.

BACKGROUND OF THE INVENTION

1. Field of the Invention

The present invention relates to a stereoscopic image observing apparatus for stereoscopically displaying an image picked-up for a medical field.

2. Description of the Related Art

Recently, an operation using an endoscope having such an advantage of low-invasiveness to a patient is widely spread in a medical field. In the operation using the endoscope, an endoscope image is a two-dimensional image and therefore it is extremely difficult to operate an operation treatment tool to the patient, compared to an operation under direct viewing.

Since a stereoscopic endoscope can display a stereoscopic image in the body cavity to the operator, it is advantageous to provide the operability which is approximate to the direct viewing by the operator. Thus, various systems of the above-mentioned stereoscopic endoscope have already been suggested.

As one example of the stereoscopic endoscopes, a head-mounted display system is suggested whereby beams from images having the parallax displayed on an image display device are directly projected onto the right and left eyes of an observer by an optical system arranged near the pole of the observer face, and image information on a large screen is equivalently and stereoscopically observed as a virtual image. As another example of the stereoscopic endoscopes, a monitor system is suggested whereby the image having the parallax is sequentially displayed on the monitor at the same position, the observer attaches an eye glass having a right and left sequential switching shutter function which is synchronous to the image sequentially switched on the monitor, and the image on the monitor is stereoscopically observed.

SUMMARY OF THE INVENTION

According to the present invention, a stereoscopic image observing apparatus comprises:
 a first projected light illuminating portion which illuminates projected light of a first image;
 a second projected light illuminating portion having the parallax to the projected light of the first image, which illuminates projected light of a second image with the illuminating axis approximately matching that of the projected light of the first image;
 a reflecting portion which applies and reflects the lens operation with the positive polarity to the projected light of the first and second images illuminated from the first projected light illuminating portion and the second projected light illuminating portion; and
 a diffusion portion arranged to the reflecting portion, which changes on time series the output positions of reflected light of the projected light of the first and second images illuminated from the first projected light illuminating portion and the second projected light illuminating portion.

BRIEF DESCRIPTION OF THE DRAWINGS

FIG. 3 is a block diagram showing the structures of an optical shift element driving device and the image projecting panel in the stereoscopic image observing apparatus according to the first embodiment of the present invention;

FIG. 4 is an explanatory diagram of a driving control signal of the image projecting panel, which is outputted from the optical shift element driving device according to the first embodiment of the present invention;

FIG. 8A is a front view showing the structure of an image projecting panel in a stereoscopic image observing apparatus according to a second embodiment of the present invention;

FIG. 8B is a cross-sectional view of the side surface of the image projecting panel;

FIG. 8C is an enlarged cross-sectional view showing a portion indicated by reference numeral 31a in the image projecting panel;

DESCRIPTION OF THE PREFERRED EMBODIMENTS

Hereinbelow, a description is given of embodiments of the present invention with reference to the drawings. First, a stereoscopic image observing apparatus will be described with reference to FIGS. 1 to 7 according to a first embodiment of the present invention.

Figure 1:
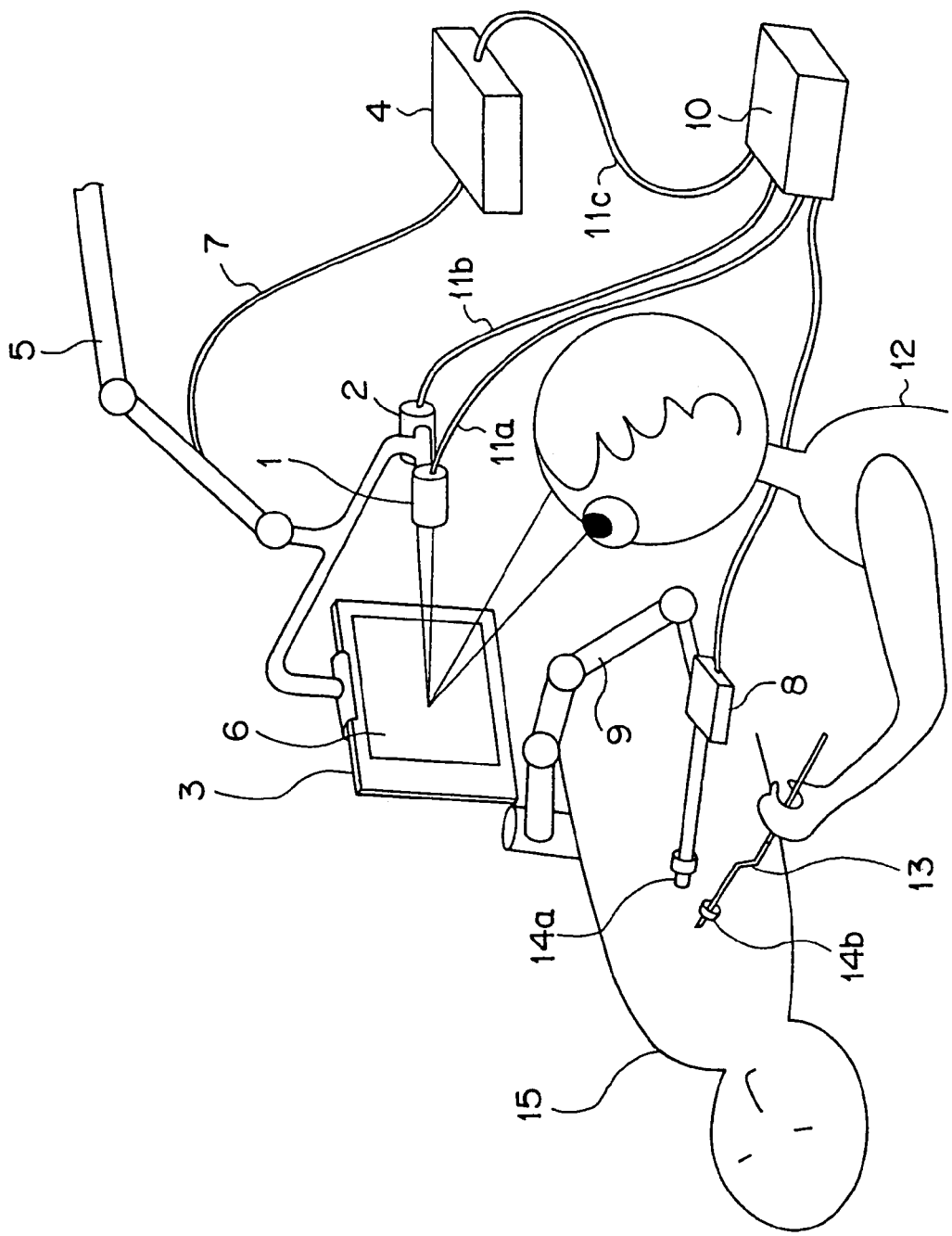
FIG. 1 is a plan view showing the entire structure of a stereoscopic image observing apparatus according to a first embodiment of the present invention.
Figure 2B:
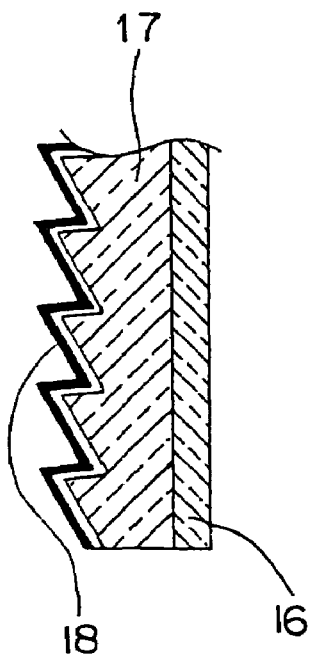
FIG. 2B is a cross-sectional view of the image projecting panel.
Figure 2A:
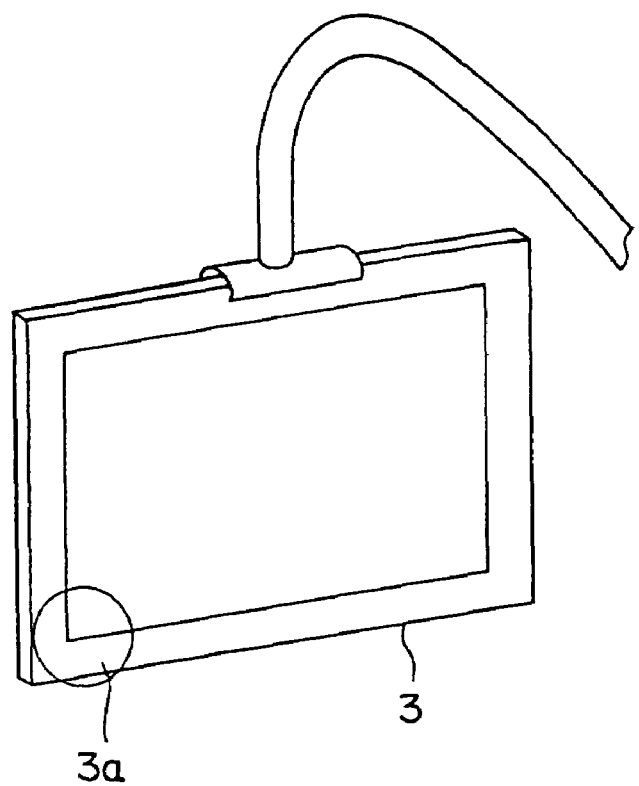
FIG. 2A is a perspective view showing the structure of an image projecting panel in the stereoscopic image observing apparatus according to the first embodiment of the present invention.
Figure 2D:
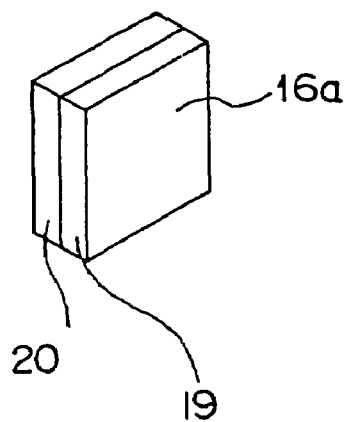
FIG. 2D is a perspective view showing an optical shift element of the image projecting panel.
Figure 2C:
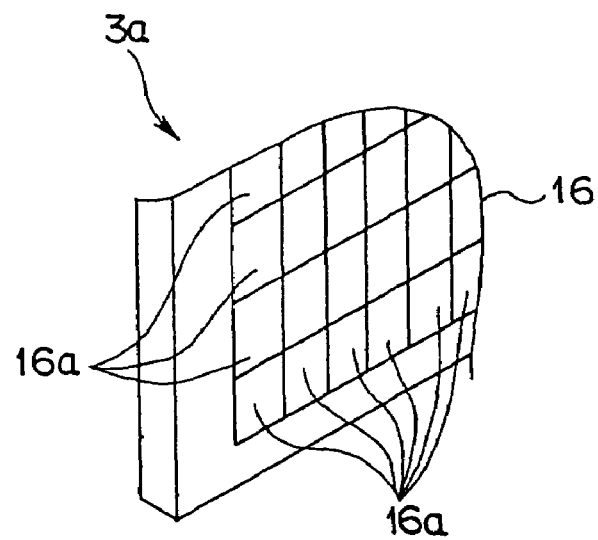
FIG. 2C is an enlarged perspective view of a portion shown by reference numeral 3a in the image projecting panel shown in FIG. 2A.
Figure 5:
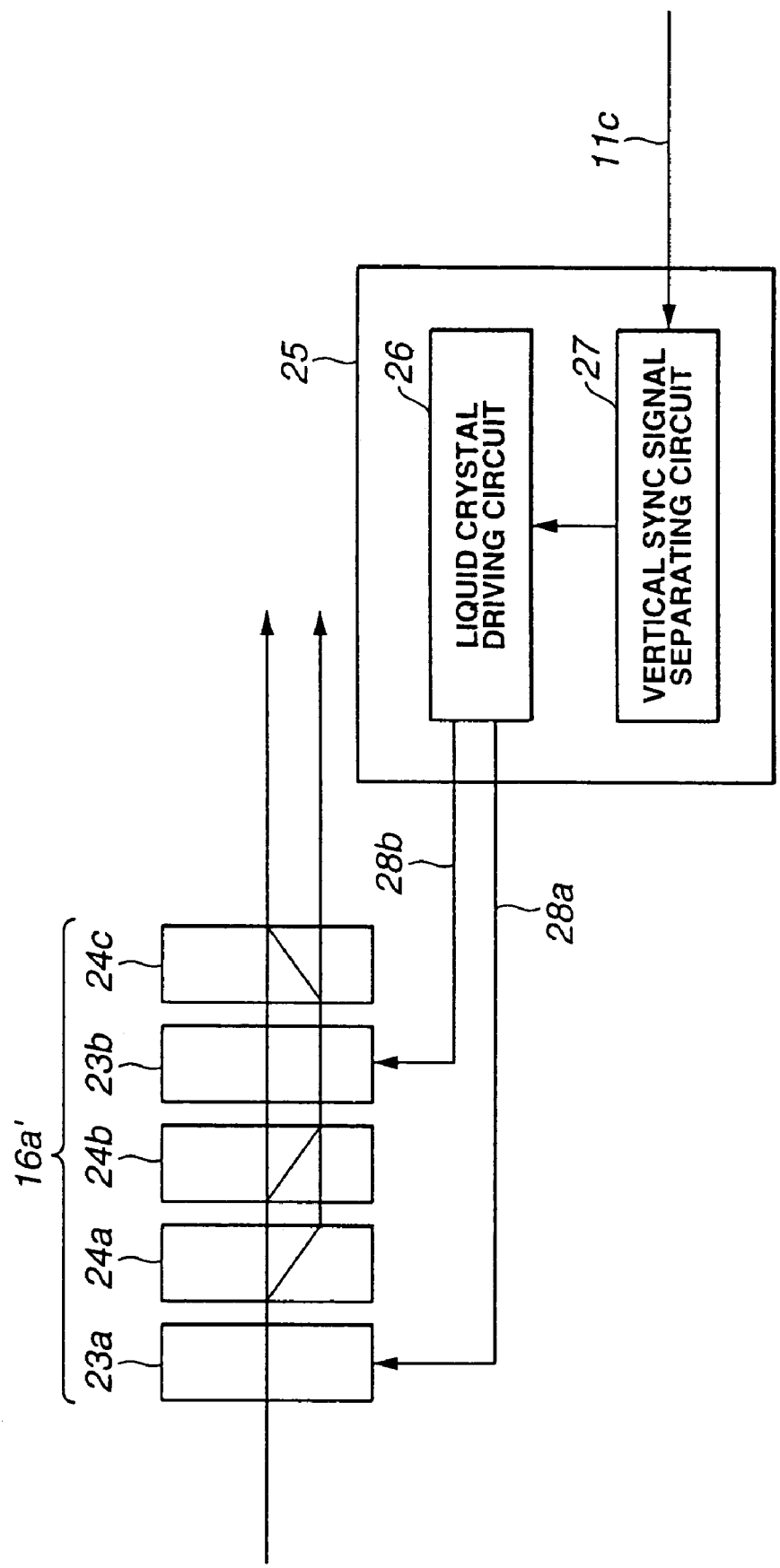
FIG. 5 is a block diagram showing an optical shift element driving device and an image projecting panel in a stereoscopic image observing apparatus according to a modification of the first embodiment of the present invention.

FIG. 1 is a plan view showing the entire structure of a stereoscopic image observing apparatus according to the first embodiment of the present invention. FIG. 2A is a perspective view showing the structure of an image projecting panel according to the first embodiment. FIG. 2B is a cross-sectional view of the image projecting panel. FIG. 2C is an enlarged perspective view of a portion shown by reference numeral 3a in the image projecting panel shown in FIG. 2A. FIG. 2D is a perspective view showing an optical shift element of the image projecting panel. FIG. 3 is a block diagram showing the structures of an optical shift element driving device and the image projecting panel in the stereoscopic image observing apparatus according to the first embodiment of the present invention. FIG. 4 is an explanatory diagram of a driving control signal of the image projecting panel, which is outputted from the optical shift element driving device according to the first embodiment of the present invention. FIG. 5 is a block diagram showing an optical shift element driving device and an image projecting panel in the stereoscopic image observing apparatus according to a modification of the first embodiment of the present invention. FIGS. 6A to 6D are explanatory diagrams of the operation of the image projecting panel in the stereoscopic image observing apparatus according to the modification of the first embodiment. FIG. 7 is an explanatory diagram of a driving control signal of the image projecting panel, which is outputted from the optical shift element driving device in the stereoscopic image observing apparatus according to the modification of the first embodiment of the present invention.

Referring to FIG. 1, a stereoscopic image observing apparatus according to the first embodiment comprises: a stereoscopic endoscope 8 which picks up and generating a stereoscopic image; a right-eye projector (hereinafter, referred to as a right-eye PJ) 1 as first projected light illuminating means which illuminates projected light of a first image that is generated based an image pick-up signal obtained by the stereoscopic endoscope 8; a left-eye projector (hereinafter, referred to as a left-eye PJ) 2 as second projected light illuminating means which illuminates projected light of a second image with a predetermined parallax to the first image illuminated from the right-eye PJ 1 and further with an illuminating axis which approximately matches that of the first image, generated based on the image pick-up signal obtained by the stereoscopic endoscope 8; and an image projecting panel 3 having a reflecting portion, to which the images for right and left eyes as the first and second images projected and illuminated from the right-eye PJ 1 and the left-eye PJ 2 are projected and which reflects the projected image light and a diffusion portion which diffuses and outputs the image light reflected from the reflecting portion. Further, the stereoscopic image observing apparatus comprises: a camera control unit (hereinafter, referred to as a CCU) 10 which controls the driving of the stereoscopic endoscope 8, performs predetermined signal processing to a stereoscopic signal that is picked up and generated, and supplies a right-eye image signal and a left-eye image signal to the right-eye PJ 1 and the left-eye PJ 2; and an optical shift element driving device 4 which controls the driving of the image projecting panel 3.

The stereoscopic endoscope 8 is attached and fixed to a supporting arm 9 having multi-joints. The stereoscopic endoscope 8 is inserted in the body cavity of the patient via a trocar 14a by an operator 12. The stereoscopic endoscope 8 obtains the image pick-up signals for right and left eyes having a predetermined parallax. The CCU 10 performs predetermined signal processing of the image pick-up signals obtained by the stereoscopic endoscope 8, and generates standard video signals, e.g., TV video signals such as an NTSC or PAL color system.

The standard video signals for right-eye and left-eye generated by the CCU 10 are supplied to the right-eye PJ 1 and the left-eye PJ 2 via signal cables 11a and 11b. The right-eye PJ 1 and the left-eye PJ 2 project the images to the image projecting panel 3.

The right-eye PJ 1, the left-eye PJ 2, and the image projecting panel 3 are attached and fixed to a supporting arm 5 having the multi-joints. The image projecting panel 3 is arranged in the sight line direction of the front upper direction in a state in which the operator 12 as an image observer is in front of a patient 15. The right-eye PJ 1 and the left-eye PJ 2 are arranged at the position for converging the projected image on the image projecting panel 3 arranged in the sight line direction of the front upper direction of the operator 12.

The projected images from the right-eye PJ 1 and the left-eye PJ 2 are displayed on the image projecting panel 3 as an image 6. The image projecting panel 3 drives the switching of the optical shift element based on an optical shift element driving signal, which will be described later, supplied via a signal cable 7 from the optical shift element driving device 4. The optical shift element driving device 4 controls the shift driving of the optical shift element of the image projecting panel 3 based on a sync signal of the standard video signal supplied from the CCU 10 via a signal cable 11c. The signal cable 7 for connecting the optical shift element driving device 4 to the image projecting panel 3 is arranged in the supporting arm 5.

The image (picked up and generated by the stereoscopic endoscope 8) 6 projected onto the image projecting panel 3 from the right-eye PJ 1 and the left-eye PJ 2 is shift-switched under the shift driving control from the optical shift element driving device 4. The projected image for right eye and the projected image for left eye are projected on the right and left eyes of the operator 12 as the observer respectively, thus recognized as stereoscopic images. The operator performs the treatment in the body cavity of the patient 15 by using a treatment tool 13 via a trocar 14b based on the stereoscopic images.

The structure of the image projecting panel 3 will be described with reference to FIGS. 2A to 2D. FIG. 2A is a perspective view of the image projecting panel 3 in the front direction. Referring to FIG. 2B, the cross section of the surface onto which the image is projected from the right-eye PJ 1 and the left-eye PJ 2 of the image projecting panel 3 comprises: an optical shift element layer 16 as a diffusion portion for temporally changing the output position of the reflected light from a Fresnel concave mirror, which will be described later, and for diffusing the reflected light; a Fresnel lens surface 17 as a Fresnel lens containing acrylic resin; and an aluminum evaporation coating 18 which is arranged to the Fresnel lens surface 17, thus forming the Fresnel concave mirror as a reflecting portion for applying the lens operation with the positive polarity to the projected light.

Referring to FIG. 2C, the optical shift element layer 16 is formed by integrating and arranging like an array a plurality of optical shift elements 16a. Referring to FIG. 2D, a double refraction plate 19 and liquid crystal 20 are adhered and formed to the plurality of optical shift elements 16a. The double refraction plate 19 has varied refraction indexes of outputted light depending on the polarization angle of the incident light. The liquid crystal 20 changes the polarization angle of the incident depending on the value of the applied voltage.

A description is given of the structure of the optical shift element driving device 4 for driving the image projecting panel 3 with the above structure with reference to FIG. 3. The optical shift element driving device 4 comprises: a vertical sync signal separating circuit 21 for separating and extracting a vertical sync signal from a sync signal included in the standard video signal generated by the CCU 10; and a liquid crystal driving circuit 22 for controlling the driving of the liquid crystal 20 in the plurality of optical shift elements 16a in the optical shit element layer 16 in the image projecting panel 3 based on the vertical sync signal separated by the vertical sync signal separating circuit 21.

That is, the images projected from the right-eye PJ 1 and the left-eye PJ 2 are transmitted through the Fresnel lens surface 17 and the optical shift element layer 16, then, are reflected by the aluminum evaporation coating 18, are enlarged by the Fresnel lens surface 17, and are outputted to the observer side from the optical shift element layer 16. Then, the liquid crystal 20 provided for the optical shift element layer 16 changes the polarization angle of the light outputted to the double refraction plate 19 depending on the value of the applied voltage. For example, when the liquid crystal driving circuit 22 does not apply the voltage to the liquid crystal 20, the polarization angle of the light outputted from the liquid crystal 20 does not change, e.g., the light at the polarization angle of 0° is outputted. On the other hand, when the liquid crystal driving circuit 22 applies a set voltage to the liquid crystal 20, the polarization angle of the light outputted from the liquid crystal 20 changes, e.g., the light at the polarization angle of 90° is outputted.

The double refraction plate 19 directly transmits and outputs the incident light at the polarization angle of 0° and the incident light at the polarization angle of 90° is refracted and outputted in the vertical down direction. That is, the image light reflected by the evaporation coating 18 is switched to have the polarization angles of 0° and 90° by the liquid crystal 20. At the polarization angles of 0° and 90°, the double refraction plate 19 directly transmits the image light at the polarization angle of 0° and the image light at the polarization angle of 90° is refracted and transmitted in the vertical down direction. Consequently, the optical shift element layer 16 diffuses and outputs the incident light (incident image).

A description is given of the operation for supplying the liquid crystal driving signal from the optical shift element driving device 4 for controlling the driving of the liquid crystal 20 with reference to FIG. 4.

The vertical sync signal separating circuit 21 in the optical shift element driving device 4 receives the standard video signal generated by the CCU 10 and separates and extracts the vertical sync signal from the video signal. When the standard video signal generated by the CCU 10 is a composite signal which is formed by superimposing the sync, signal to the video signal, the vertical sync signal separating circuit 21 separates the video signal and a composite sync signal from the composite signal, and extracts and separates the vertical sync signal from the separated composite sync signal. When the standard video signal generated by the CCU 10 is a component signal which individually transmits the video signal and the composite sync signal, the vertical sync signal separating circuit 21 separates and extracts the vertical sync signal from the composite sync signal which is individually transmitted.

Based on the vertical sync signal separated by the vertical sync signal separating circuit 21, the liquid crystal driving circuit 22 generates and outputs a liquid crystal driving signal at the timing synchronous with the vertical sync signal. With respect to a relationship between the vertical sync signal and the liquid crystal driving signal, when the standard video signal generated by the CCU 10 is an NTSC color system, referring to FIG. 4, the period of the vertical sync signal as one field for displaying one image is 1/60 sec, and the liquid crystal driving circuit 22 outputs the liquid crystal driving signal for alternately on/off operating the liquid crystal 20 synchronously with the one field period. That is, with respect to the relationship between the vertical sync signal and the liquid crystal driving signal, a predetermined voltage is applied to the liquid crystal 20 for the period of the on-operation of the liquid crystal driving signal synchronous with the vertical sync signal, and the application of the predetermined voltage to the liquid crystal 20 is stopped for the period of the off-operation of the liquid crystal driving signal, thus to switch the polarization angles of the light outputted from the liquid crystal 20.

That is, the image light is outputted from the right-eye PJ 1 and left-eye PJ 2, and is reflected by the aluminum evaporation coating 18 in the image projecting panel 3. The image light is enlarged by the Fresnel lens surface 17, thereby forming the projected image. The projected image is polarized by the liquid crystal 20 in the optical shift element layer 16 for every field, and is accurately diffused in the vertical direction by the double refraction plate 19.

Consequently, it is possible to display, as a clear stereoscopic image without roughness, the image 6 displayed on the image projecting panel 3 which is observed by the observer as the operator 12.

Next, a description is given of a stereoscopic image observing apparatus according to a modification of the first embodiment of the present invention with reference to FIGS. 5 to 7. According to the modification of the first embodiment, the structure is different from that of the optical shift elements 16a which forms the optical shift element layer 16 in the image projecting panel 3 according to the first embodiment as mentioned above. The optical shift element 16a comprises the liquid crystal 20 and the double refraction plate 19, and diffuses the projected image in the vertical direction.

Referring to FIG. 5, an optical shift element 16a' according to the modification diffuses the projected image in the horizontal and vertical direction and therefore the optical shift element 16a' comprises: a first liquid crystal 23a and a second liquid crystal 23b; a first double refraction plate 24a and a second double refraction plate 24b arranged between the two liquid crystal 23a and 23b; and a third double refraction plate 24c arranged on the output side of the second liquid crystal 23b. Further, an optical shift element driving device 25 having a liquid crystal driving circuit 26 and a vertical sync signal separating circuit 27 is connected to the first and second liquid crystal 23a and 23b in the optical shift element 16a' via signal cables 28a and 28b.

The first liquid crystal 23a and the second liquid crystal 23b use the same characteristic. Similarly to the first embodiment, the polarization angles of the first liquid crystal 23a and second liquid crystal 23b do not change (polarization angle of 0°) upon the off-operation for applying no voltage. The polarization angle of the first liquid crystal 23a and second liquid crystal 23b change (the polarization angle of 90°) upon the on-operation for applying the set voltage.

The first to third double refraction plates 24a to 24c have varied double refraction characteristics. The first double refraction plate 24a straightly transmits the incident light at the polarization angle of 0° and refracts the incident light at the polarization angle of 90° in the oblique left down direction of the advance direction of light. The second double refraction plate 24b refracts the incident light at the polarization angle of 0° in the vertical down direction of the advance direction of light and straightly transmits the incident light at the polarization angle of 90°. The third double refraction plate 24c straightly transmits the incident light at the polarization angles of 0° and 180° and refracts the incident light at the polarization angle of 90° in the vertical up direction of the advance direction of light.

A description is given of the operation for the optical shift in the horizontal and vertical direction of the optical shift element 16a' with the above-mentioned structure, namely, the operation for diffusing the image with reference to FIGS. 6A to 6D. FIGS. 6A to 6D show the optical shift operation by four combinations of on- and off-operation of the voltage applied to the first liquid crystal 23a and second liquid crystal 23b.

Figure 6A:
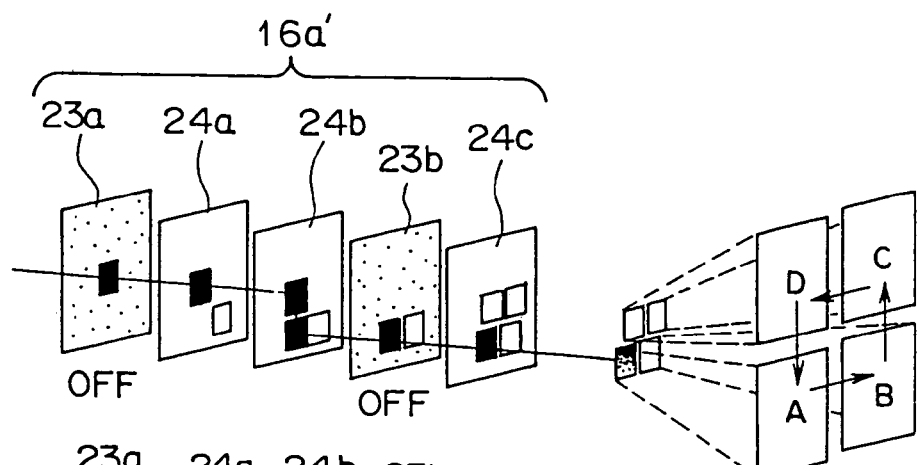
FIG. 6A is an explanatory diagram of the operation of the image projecting panel in the stereoscopic image observing apparatus according to the modification of the first embodiment, showing a light transmitting state upon switching off voltages applied to both first liquid crystal and second liquid crystal.
Figure 7:
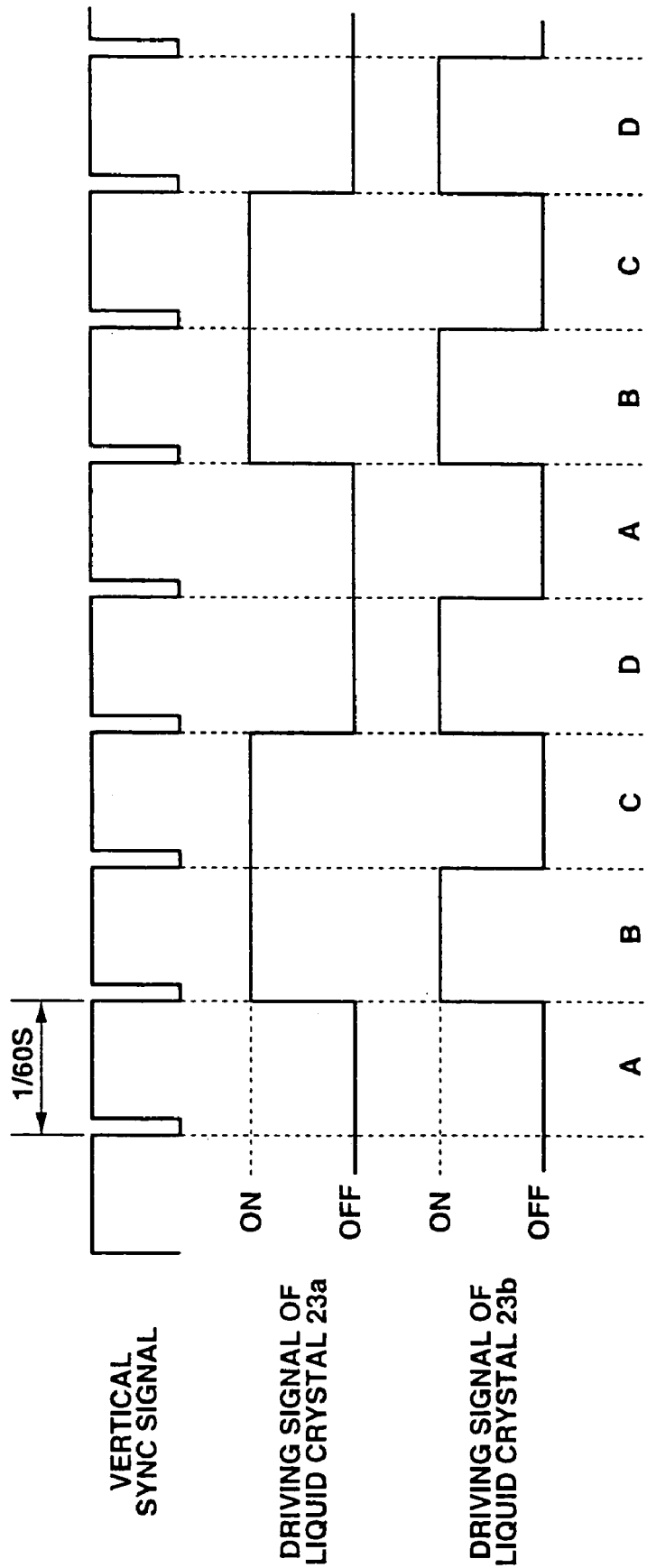
FIG. 7 is an explanatory diagram of a driving control signal of the image projecting panel, which is outputted from the optical shift element driving device in the stereoscopic image observing apparatus according to the modification of the first embodiment of the present invention.

FIG. 6A shows a transmitting state of light upon the off-operation of the voltage applied to the first liquid crystal 23a and second liquid crystal 23b. The light at the polarization angle 0° outputted from the first liquid crystal 23a, to which the applied voltage is off, is incident on the first double refraction plate 24a and the second double refraction plate 24b. The light incident on the first double refraction plate 24a and second double refraction plate 24b straightly transmits the first double refraction plate 24a with the above-mentioned double refraction characteristic, and is refracted in the vertical down direction of the advance direction of light through the second double refraction plate 24b. Since the second liquid crystal 23b is in the off-state, the light at the polarization angle of 0° refracted in the vertical down direction by the second double refraction plate 24b does not change its polarization angle. The light at the polarization angle of 0° is outputted to the third double refraction plate 24c. With the double refraction characteristic of the third double refraction plate 24c, the light at the polarization angle of 0° is straightly transmitted and therefore the image outputted from the optical shift element 16a' is at a position shown by reference numeral A in FIG. 6A.

Figure 6B:
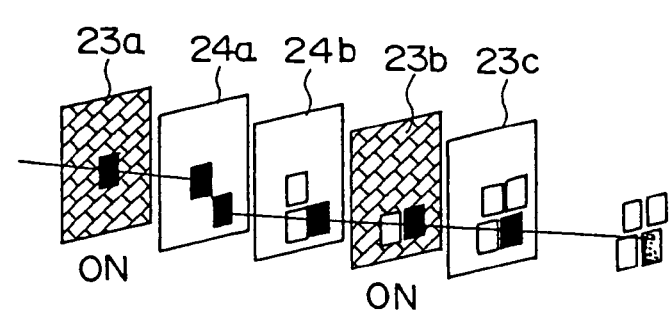
FIG. 6B is an explanatory diagram showing a state of switching on the voltage applied to both the first liquid crystal and second liquid crystal.

FIG. 6B shows a light transmitting state when the on-operation of the applied voltage is set to both the first liquid crystal 23a and second liquid crystal 23b. The light at the polarization angle of 90° outputted from the first liquid crystal 23a upon the on-operation of the applied voltage is incident on the first double refraction plate 24a and the second double refraction plate 24b. The light at the polarization angle of 90° incident on the first double refraction plate 24a and second double refraction plate 24b is refracted in the oblique left down direction of the advance direction of light through the first double refraction plate 24a with the above-mentioned double refraction characteristic, and is straightly transmitted through the second double refraction plate 24b. Since the second liquid crystal 23b is in the on-state, the light at the polarization angle of 90° straightly transmitted through the second double refraction plate 24b is further polarized at the angle of 90° and thus the light at the polarization angle of 180° is outputted to the third double refraction plate 24c. With the double refraction characteristic of the third double refraction plate 24c, the light at the polarization angle of 180° is straightly transmitted. Therefore, the image outputted from the optical shift element 16a' is at the position shown by reference numeral B in FIG. 6B.

Figure 6C:
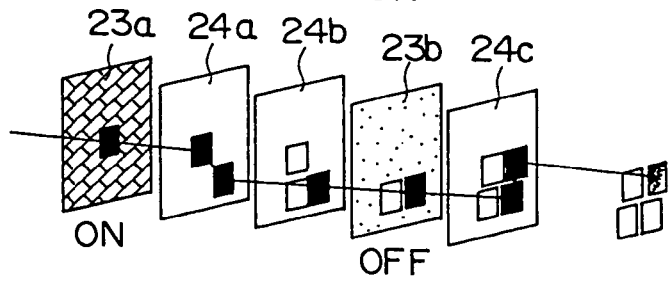
FIG. 6C is an explanatory diagram showing a state of switching on the voltage applied to the first liquid crystal and of switching off the voltage applied to the second liquid crystal.

FIG. 6C shows the first liquid crystal 23a in the on-operation of the applied voltage and the second liquid crystal 23b in the off-operation of the applied voltage. The light at the polarization angle of 90° outputted from the first liquid crystal 23a in the on-operation of the applied voltage is incident on the first double refraction plate 24a and the second double refraction plate 24b. The light at the polarization angle of 90° incident on the first double refraction plate 24a and second double refraction plate 24b is refracted in the oblique left down direction of the advance direction of light through the first double refraction plate 24a with the above-mentioned double refraction characteristic, and is straightly transmitted through the second double refraction plate 24b. The light at the polarization angle of 90° straightly transmitted through the second double refraction plate 24b is outputted to the third double refraction plate 24c at the polarization angle of 90° because the second liquid crystal 23b is in the off-operation. With the double refraction characteristic of the third double refraction plate 24c, the light at the polarization angle of 90° is refracted in the vertical up direction of the advance direction of light. Thus, the image outputted from the optical shift element 16a' is at the position shown by reference numeral C in FIG. 6C.

Figure 6D:
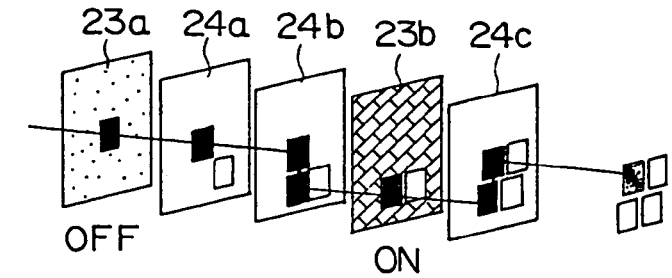
FIG. 6D is an explanatory diagram showing a state of switching off the voltage applied to the first liquid crystal and of switching on the voltage applied to the second liquid crystal.

FIG. 6D shows the first liquid crystal 23a in the off-operation of the applied voltage and the second liquid crystal 23b in the on-operation of the applied voltage. The light at the polarization angle of 0° outputted from the first liquid crystal 23a in the off-operation of the applied voltage is incident on the first double refraction plate 24a and the second double refraction plate 24b. With the double refraction characteristic, the light at the polarization angle of 0° incident on the first double refraction plate 24a and second double refraction plate 24b is straightly transmitted through the first double refraction plate 24a and is refracted in the vertical down direction of the advance direction of light through the second double refraction plate 24b. Since the second liquid crystal 23b is in the on-operation, the light at the polarization angle of 0° refracted in the vertical down direction through the second double refraction plate 24b is polarized at the angle of 90°, and is outputted to the third double refraction plate 24c. With the double refraction characteristic of the third double refraction plate 24c, the light at the polarization angle of 90° is refracted in the vertical up direction of the advance direction of light and therefore the image outputted from the optical shift element 16a' is at a position shown by reference numeral D in FIG. 6D.

As mentioned above, the optical shift (diffusion) is possible in the horizontal and vertical directions by controlling the on/off driving on the time series of the first liquid crystal 23a and the second liquid crystal 23b in the optical shift element 16a'.

A description is given of the liquid crystal driving signal which is outputted from the liquid crystal driving circuit 26 in the optical shift element driving device 25 for controlling the driving of the first liquid crystal 23*a* and the second liquid crystal 23*b* with reference to FIG. 7.

Similarly to the first embodiment, the vertical sync signal is separated and extracted from the video signal outputted from the CCU 10 and, synchronously with the vertical sync signal, the driving signal of the first liquid crystal 23*a* and the driving signal of the second liquid crystal 23*b* are generated.

The driving signal of the first liquid crystal 23*a* and the driving signal of the second liquid crystal 23*b* need to shift the polarization angle to the four ones. Thus, one status corresponds to the period of one field for displaying one image. For example, in the case of the video signal of the NTSC color system, for the first one field period of 1/60 sec, the driving signal for the off-operation of the first liquid crystal 23*a* and the second liquid crystal 23*b* is generated. For the second one field period of 1/60 sec, the driving signal for the on-operation of the first liquid crystal 23*a* and the second liquid crystal 23*b* is generated. For the third one field period of 1/60 sec, the driving signal for the on-operation of the first liquid crystal 23*a* and for the off-operation of the second liquid crystal 23*b* is generated. For the fourth one field period of 1/60 sec, the driving signal for the off-operation of the first liquid crystal 23*a* and for on-operation of the second liquid crystal 23*b* is generated.

That is, synchronously with the vertical sync signal, the optical shift (diffusion) is possible for one cycle corresponding to the four fields in the horizontal and vertical directions. Therefore, the operator 12 as the observer can observe the clear stereoscopic image without roughness from the image projecting panel 3.

According to the first embodiment of the present invention and the modification thereof, the optical shift period is one field. However, it can be as follows. That is, according to the optical shift operation in two vertical directions, the inputted image signal is scan-converted at the double speed. According to the optical shift operation in the horizontal and vertical directions, the inputted image signal is scan-converted at the four-time speed. Consequently, the image is diffused for every field as the period of the optical shift operation without flickering.

The image projecting panel 3 contains an optical member and a resin member and therefore the sterilization by radiation rays is possible. The image projecting panel 3 can be positioned in the sight-line up direction of the operator 12 in an operation room as a sterilization area.

Figure 9:
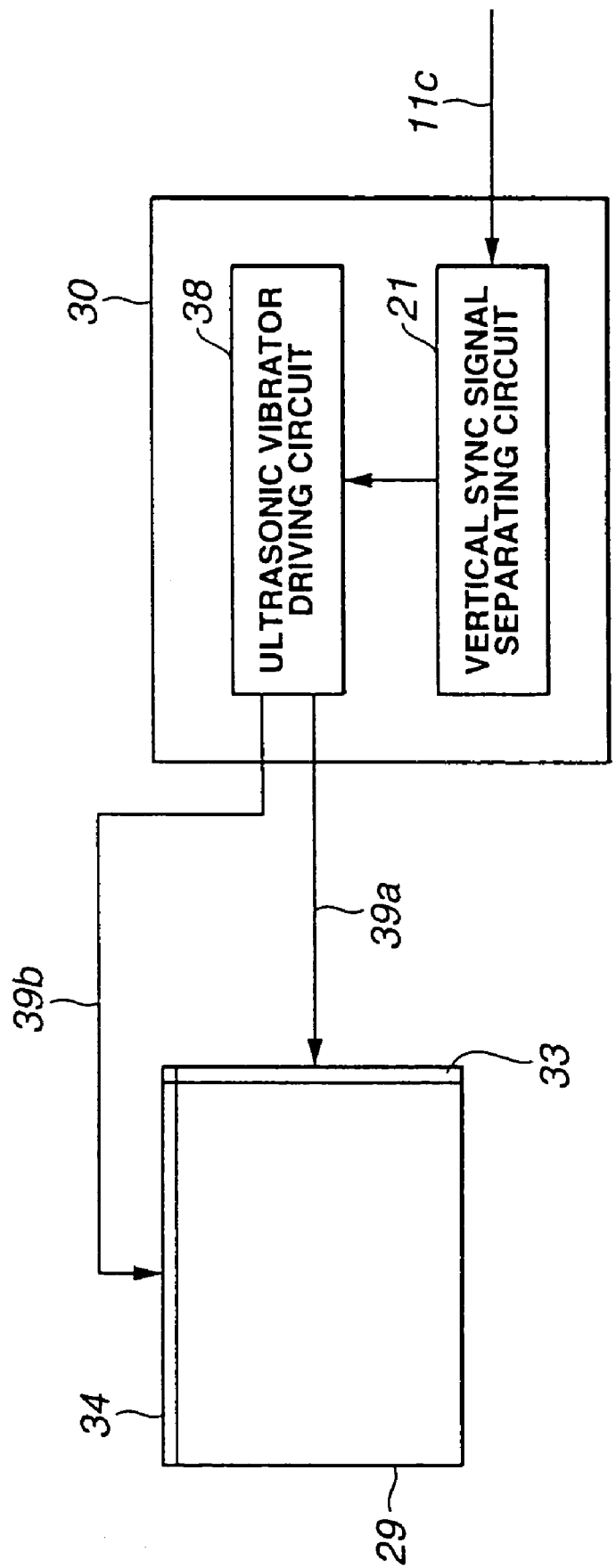
FIG. 9 is a block diagram showing the structure of an ultrasonic vibrating element driving device in the stereoscopic image observing apparatus according to the second embodiment of the present invention.
Figure 10:
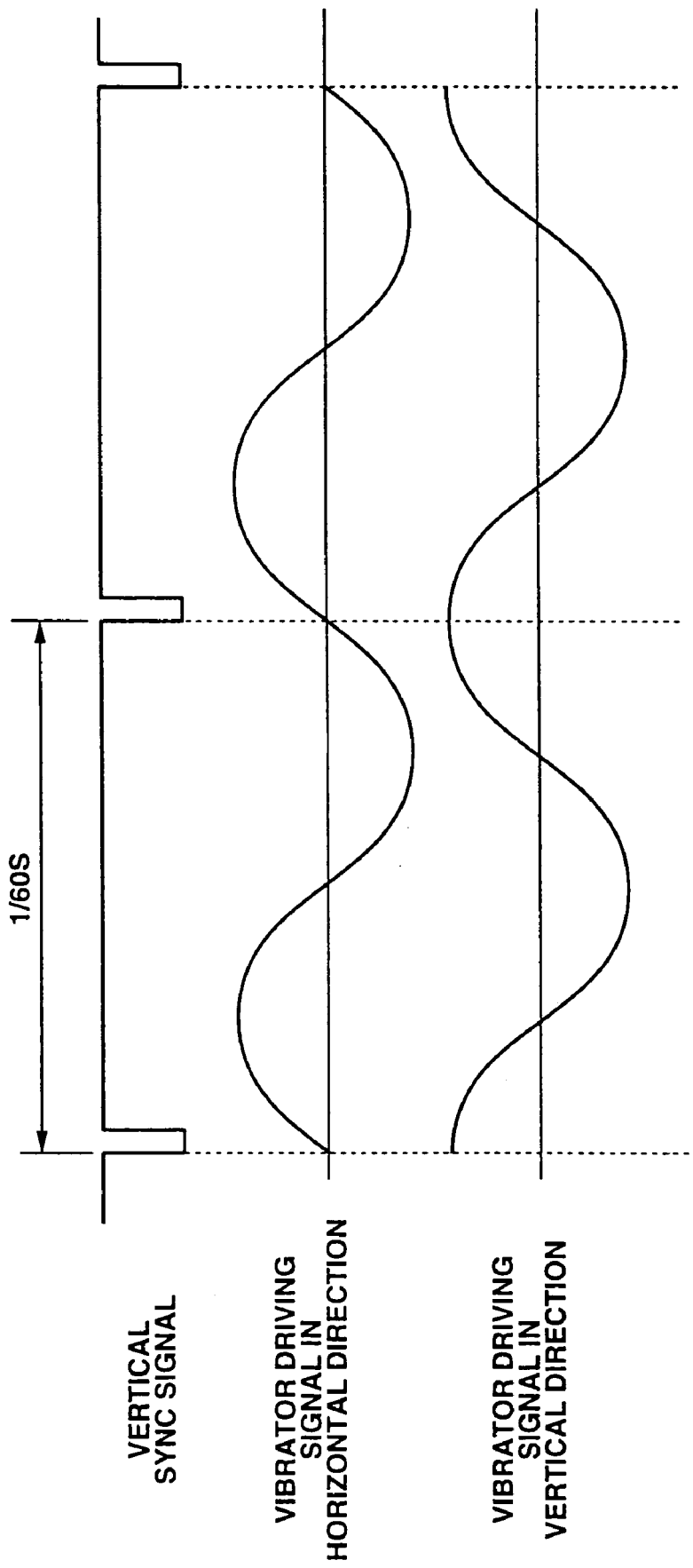
FIG. 10 is an explanatory diagram of a driving signal of an ultrasonic vibrator, which is outputted from the ultrasonic vibrating element driving device in the stereoscopic image observing apparatus according to the second embodiment of the present invention.

Next, a description is given of a stereoscopic image observing apparatus according to a second embodiment of the present invention with reference to FIGS. 8A to 11. FIGS. 8A to 8C show the structure of an image projecting panel in a stereoscopic image observing apparatus according to the second embodiment of the present invention, FIG. 8A is a front view showing the image projecting panel, FIG. 8B is a cross-sectional view showing the side surface of the image projecting panel, and FIG. 8C is an enlarged cross-sectional view showing a portion indicated by reference numeral 31*a* in the image projecting panel shown in FIG. 8B. FIG. 9 is a block diagram showing the structure of an ultrasonic vibrating element driving device in the stereoscopic image observing apparatus according to the second embodiment of the present invention. FIG. 10 is an explanatory diagram of a driving signal of an ultrasonic vibrator, which is outputted from the ultrasonic vibrating element driving device in the stereoscopic image observing apparatus according to the second embodiment of the present invention. FIGS. 11A to 11C show the structure of an image projecting panel in a stereoscopic image observing apparatus according to a modification of the second embodiment of the present invention, FIG. 11A is a front view showing the image projecting panel, FIG. 11B is a side view showing the image projecting panel, and FIG. 11C is an enlarged cross-sectional view showing a portion indicated by reference numeral 41*a* in the image projecting panel shown in FIG. 11B.

The stereoscopic image observing apparatus according to the second embodiment has the image projecting panel 3 different from that according to the first embodiment.

Upon reflecting and projecting the projected images from the right-eye PJ 1 and the left-eye PJ 2, the image projecting panel 3 according to the first embodiment polarizes the angle of the reflected and projected images by the liquid crystal 20, and the polarized and projected image light is diffused by the double refraction plate 19. On the other hand, an image projecting panel 29 according to the second embodiment includes ultrasonic vibrators in the vertical and horizontal directions. The ultrasonic vibrators ultrasonically vibrate a light diffusion plate in the horizontal and vertical directions, thus to diffuses the light.

Referring to FIGS. 8A to 8C, the image projecting panel 29 comprises: a Fresnel concave mirror 32 which reflects the light projected from the right-eye PJ 1 and the left-eye PJ 2; a light diffusion plate 31 for projecting and diffusing the reflected light; a horizontal driving ultrasonic vibrator 33 arranged to the side of the light diffusion plate 31 shown on the right side in FIGS. 8A to 8C; and a vertical driving ultrasonic vibrator 34 arranged to the side of the light diffusion plate 31 shown on the upper side in FIGS. 8A to 8C.

The light diffusion plate 31 contains an acrylic member and comprises a diffusion surface 37 with a minute uneven portion, having its surface to which bead resin with the small diameter is driven or which is roughly formed.

The Fresnel concave mirror 32 is arranged on the back of the light diffusion plate 31. The aluminum evaporation coating 18 is applied to the Fresnel lens surface 17 on the back of the Fresnel concave mirror 32. The light diffusion plate 31 is arranged to the surface of the Fresnel concave mirror 32 to be vibrated in the horizontal and vertical directions.

A fixing plate 35 is arranged to the end of the Fresnel concave mirror 32 on the right end shown in FIGS. 8A to 8C. The fixing plate 35 fixes and arranges the horizontal driving ultrasonic vibrator 33 between the fixing plate 35 and the right side of the light diffusion plate 31 shown in FIG. 8B which is arranged to the surface of the Fresnel concave mirror 32 to be vibrated. An elastic fixing plate 36 is arranged to the left ends of the Fresnel concave mirror 32 and the light diffusion plate 31 shown in FIG. 8B. That is, the horizontal driving ultrasonic vibrator 33 is vibrated in the horizontal direction in FIG. 8B, thereby transmitting the generated vibrations to the light diffusion plate 31. Further, the light diffusion plate 31 is ultrasonically vibrated in the horizontal direction because another end of the light diffusion plate 31 is fixed to an elastic fixing plate 36.

The vertical driving ultrasonic vibrator 34 is attached and fixed to the side of the light diffusion plate 31 on the upper side shown in FIG. 8A, similarly to the horizontal driving ultrasonic vibrator 33 (not shown in detail). The ultrasonic vibration of the vertical driving ultrasonic vibrator 34 ultrasonically vibrates the light diffusion plate 31 in the vertical direction.

The horizontal driving ultrasonic vibrator 33 and the vertical driving ultrasonic vibrator 34 use a bolted Langevin vibrator, and the elastic fixing plate 36 uses a plate spring. That is, the horizontal driving ultrasonic vibrator 33 and the vertical driving ultrasonic vibrator 34 arranged to the image projecting panel 29 have elastic axes in the surface direction of the light diffusion plate 31. The image projecting panel 29 is fixed, by the fixing plate 35, to the one side of the light diffusion plate 31 overlaid to the Fresnel concave mirror 32 in the horizontal and vertical directions via the horizontal driving ultrasonic vibrator 33 and the vertical driving ultrasonic vibrator 34. Other ends of the light diffusion plate 31 and the Fresnel concave mirror 32 in the horizontal and vertical directions are fixed by the elastic fixing plate 36. Therefore, voltages in the positive and negative directions are applied to the horizontal driving ultrasonic vibrator 33 and the vertical driving ultrasonic vibrator 34 and then the light diffusion plate 31 is slidably vibrated to the Fresnel concave mirror 32. Consequently, the position of the light diffusion plate 31 relatively changes.

Next, a description is given of an ultrasonic vibrator driving device 30 for controlling the driving of the image projecting panel 29 having the horizontal driving ultrasonic vibrator 33 and the vertical driving ultrasonic vibrator 34 with reference to FIG. 9.

The ultrasonic vibrator driving device 30 comprises: an ultrasonic vibrator driving circuit 38 and the vertical sync signal separating circuit 21. Similarly to the first embodiment, the vertical sync signal separating circuit 21 separates and extracts the vertical sync signal from the composite sync signal forming the standard video signal outputted from the CCU 10. The ultrasonic vibrator driving circuit 38 generates ultrasonic vibrator driving signals for driving the horizontal driving ultrasonic vibrator 33 and the vertical driving ultrasonic vibrator 34 based on the vertical sync signal separated by the vertical sync signal separating circuit 21, and supplies the generated ultrasonic vibrator driving signals to the horizontal driving ultrasonic vibrator 33 and the vertical driving ultrasonic vibrator 34 via signal cables 39*a* and 39*b*.

Referring to FIG. 10, the ultrasonic vibrator driving signals are synchronized with the vertical sync signal extracted by the vertical sync signal separating circuit 21, and then the ultrasonic vibrator driving signals are generated. Since the horizontal driving ultrasonic vibrator 33 and the vertical driving ultrasonic vibrator 34 use the bolted Langevin vibrator, the voltages in the positive and negative directions are applied to the horizontal driving ultrasonic vibrator 33 and the vertical driving ultrasonic vibrator 34 and then they are expanded and contracted with amplitudes in accordance with the applied voltages in the elastic-axis directions thereof.

The light diffusion plate 31 applies sine waves whose phases are deviated at an angle of 90°, to the horizontal driving ultrasonic vibrator 33 and the vertical driving ultrasonic vibrator 34 and, thus, the light diffusion plate 31 circularly moves to the Fresnel concave mirror 32.

Specifically, the sine waves are generated for periods matching the period of 1/60 sec of the vertical sync signal having one field period for displaying one image. Further, from the driving signal of the vertical driving ultrasonic vibrator 34, a sine wave driving signal whose phase advances at the angle of 90° from the driving signal of the horizontal driving ultrasonic vibrator 33 is generated.

According to the second embodiment, the sine wave driving signals are applied to the horizontal driving ultrasonic vibrator 33 and the vertical driving ultrasonic vibrator 34, thereby vibrating the light diffusion plate 31 to the Fresnel concave mirror 32. As a result, the image reflected by the light diffusion plate 31 and the Fresnel concave mirror 32 is observed as the stereoscopic image by the operator 12 as the observer, and the roughness as the factor for deteriorating the image quality of the observed image is reduced.

Figure 11:
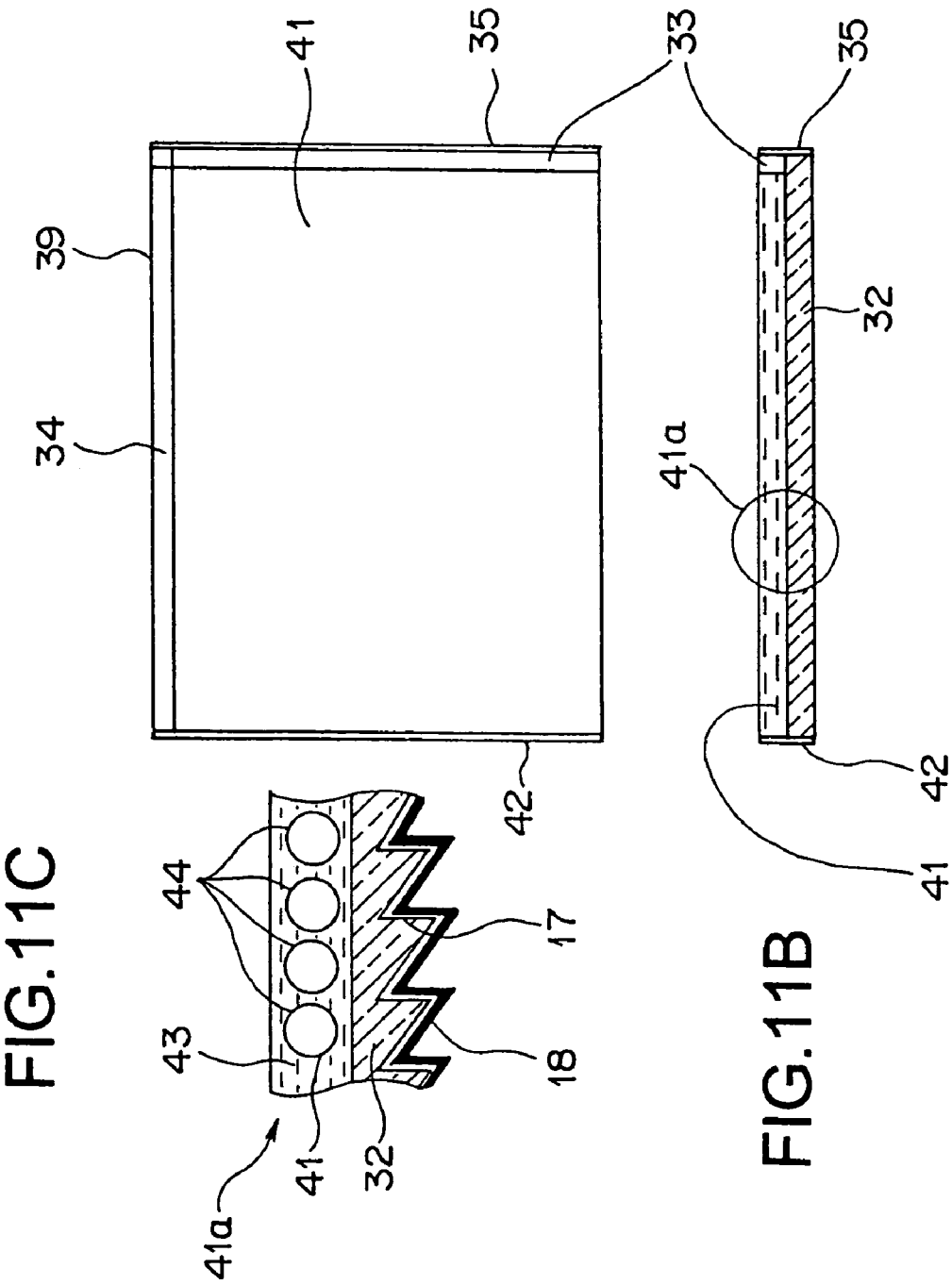
FIG. 11A is a front view showing the structure of the image projecting panel in the stereoscopic image observing apparatus according to the second embodiment of the present invention.
FIG. 11B is a side view of the image projecting panel.
FIG. 11C is an enlarged cross-sectional view showing a portion indicated by reference numeral 41a in the image projecting panel.

Next, a description is given of a stereoscopic image observing apparatus according to a modification of the second embodiment with reference to FIG. 11. According to the modification, an image projecting panel 39 is used, instead of the image projecting panel 29 used for the stereoscopic image observing apparatus according to the second embodiment.

The surface of the light diffusion plate 31 in the image projecting panel 29 has the diffusion surface 37 having the minute uneven portion. On the contrary, a light diffusion layer 41 which seals fluid 43 and beads 44 is arranged to the image projecting panel 39 according to the modification of the second embodiment. Similarly to the second embodiment, the horizontal driving ultrasonic vibrator 33 and the vertical driving ultrasonic vibrator 34 are arranged to one side of the light diffusion layer 41 in the horizontal and vertical directions. A fixing plate 42 fixes, with the Fresnel concave mirror 32, the side of the light diffusion layer 41 on the opposite side of the joint end of the horizontal driving ultrasonic vibrator 33 and the vertical driving ultrasonic vibrator 34 of the light diffusion layer 41.

The fluid 43 of the light diffusion layer 41 contains a transparent member with low viscosity, e.g., water. The beads 44 contain a resin member having the refractive index different from that of the fluid 43. According to the modification of the second embodiment, the ultrasonic vibrator driving device 30 drives the horizontal driving ultrasonic vibrator 33 and the vertical driving ultrasonic vibrator 34 of the light diffusion layer 41, thereby applying the ultrasonic vibration to the fluid 43 and the beads 44 in the light diffusion layer 41.

According to the modification of the second embodiment, the beads 44 sealed in the light diffusion layer 41 are slightly vibrated, the image light reflected from the Fresnel concave mirror 32 is diffused, and the stereoscopic image can be observed by the operator 12 as the observer. Therefore, according to the modification, the roughness as the factor for deteriorating the image quality is reduced. Further, according to the modification, the light diffusion layer 41 and the Fresnel concave mirror 32 do not need to relatively move and therefore the control of ultrasonic vibrations is easy and the mechanical strength is improved.

Figure 12:
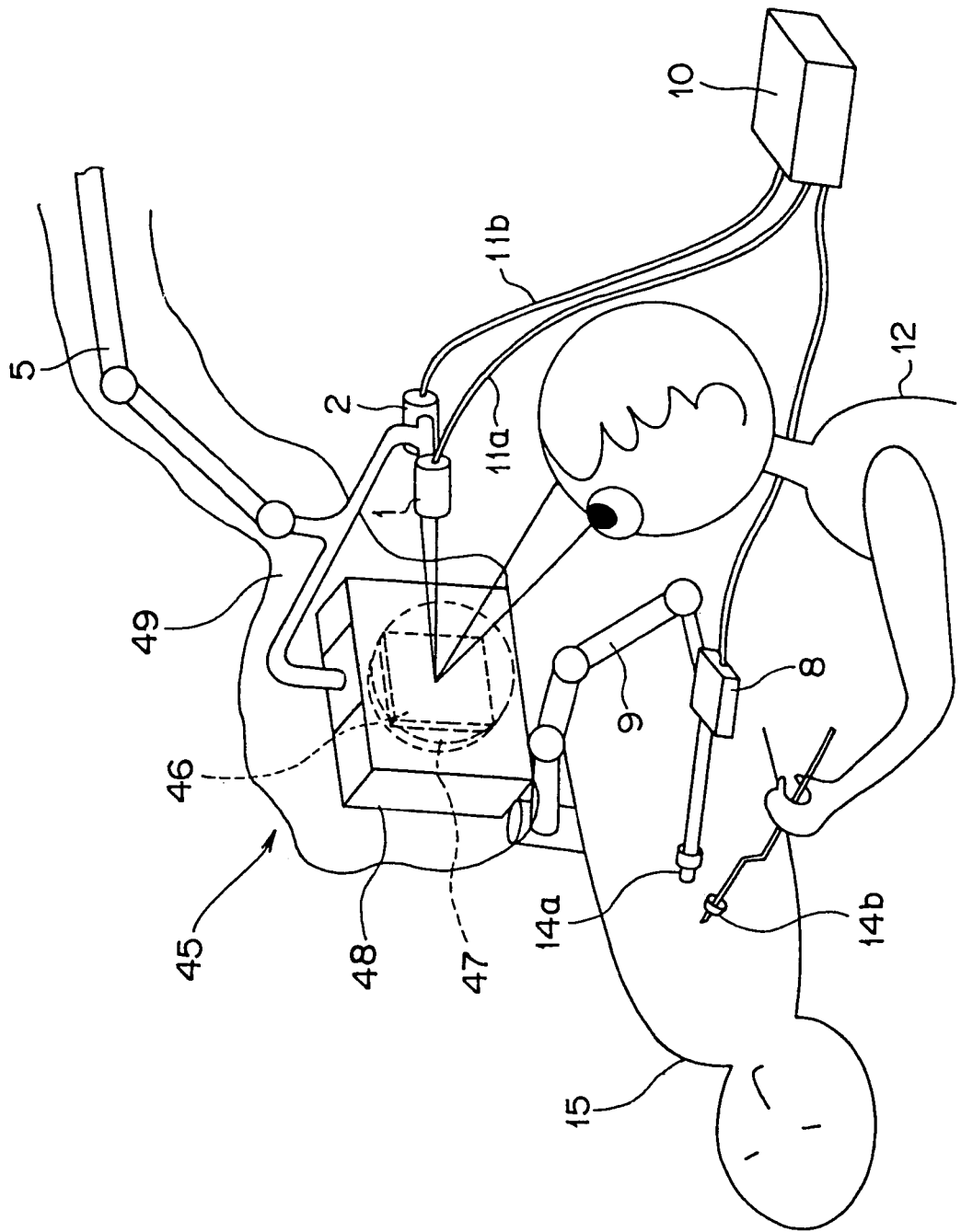
FIG. 12 is a block diagram showing the entire structure of a stereoscopic image observing apparatus according to a third embodiment of the present invention.
Figure 13:
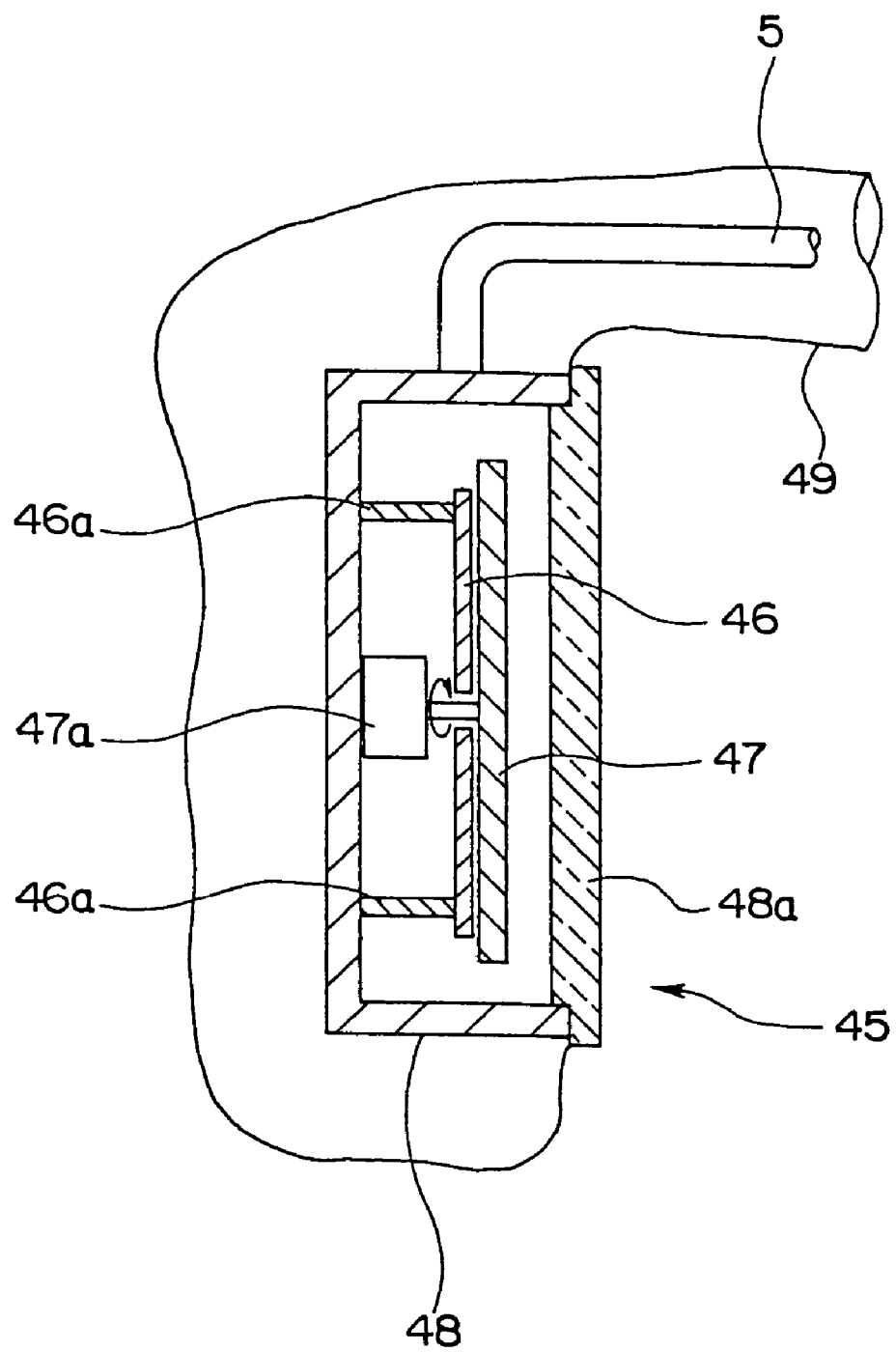
FIG. 13 is a cross-sectional view showing the structure of an image projecting panel according to the third embodiment of the present invention.

Next, a description is given of a stereoscopic image observing apparatus according to a third embodiment of the present invention with reference to FIGS. 12 and 13. FIG. 12 is a block diagram showing the entire structure of a stereoscopic image observing apparatus according to the third embodiment of the present invention. FIG. 13 is a cross-sectional view showing the structure of an image projecting panel in the stereoscopic image observing apparatus according to the third embodiment of the present invention. The same components as those shown in FIG. 1 are designated by the same reference numerals and a detailed description thereof is omitted.

According to the third embodiment, the stereoscopic image observing apparatus comprises an image projecting panel 45 comprising: a Fresnel concave mirror 46; a light diffusion plate 47 arranged to the front surface of the Fresnel concave mirror 46; a case 48 including the Fresnel concave mirror 46 and the light diffusion plate 47; and a sterilization drape 49 for covering the case 48, in place of the image projecting panel 3 according to the first embodiment.

Referring to FIG. 13, in the image projecting panel 45, the Fresnel concave mirror 46, which is subjected to the aluminum evaporation coating to the Fresnel lens surface, is fixed to the inside of the back surface of the case 48 via a plurality of fixing tools 46*a*. The light diffusion plate 47 is circularly formed with the minute-uneven surface in front of the Fresnel concave mirror 46. A diffusion plate rotating mechanism portion 47*a* is fixed in the center of the light diffusion plate 47.

The diffusion plate rotating mechanism portion 47a comprises a DC motor. The rotating shaft of the DC motor pierces through the center of the Fresnel concave mirror 46 and is fixed to the light diffusion plate 47. That is, according to the third embodiment, the light diffusion plate 47 is rotated by rotating the DC motor of the diffusion plate rotating mechanism portion 47a.

A transparent sterilized acrylic plate 48a is detachably arranged to the front surface of the case 48. The case 48 and the end surface of the sterilization drape 49 for covering the supporting arm 5 which attaches and fixes the case 48 are sandwiched and fixed between the acrylic plate 48a and the case 48.

According to the third embodiment, the images for the right and left eyes are projected to the image projecting panel 45 from the right-eye PJ 1 and the left-eye PJ 2. Then, the images for the right and left eyes are enlarged, reflected, and projected by the Fresnel concave mirror 46. The enlarged and projected images for the right and left eyes are diffused and outputted to the both eyes of the operator 12 as the observer with the enlarged pupil diameter upon transmitting the images through the light diffusion plate 47 which is rotated by the diffusion plate rotating mechanism portion 47a.

The image projecting panel 45 covered with the sterilization drape 49 can be used in the sterilized area such as an operation room, the roughness of the projected image is reduced by the light diffusion plate 47 which is rotated, and the stereoscopic image can be observed with preferable image quality.

The diffusion plate rotating mechanism portion 47a may be, for example, an air turbine as well as the DC motor, and the light diffusion plate 47 may be rotated by transmitting air to the air turbine by a compressor (not shown).

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. A stereoscopic image observing apparatus comprising:
   a first projected light illuminating portion which illuminates projected light of a first image;
   a second projected light illuminating portion having a parallax to the projected light of the first image, wherein the second projected light illuminating portion illuminates projected light of a second image with an illuminating axis approximately matching that of the projected light of the first image;
   a reflecting portion which applies and reflects the lens operation with a positive polarity to the projected light of the first and second images illuminated from the first projected light illuminating portion and the second projected light illuminating portion;
   a diffusion portion arranged in front of the reflecting portion, the diffusion portion including a light diffusion plate for diffusing the output positions of reflected light of the projected light of the first and second images illuminated from the first projected light illuminating portion and the second projected light illuminating portion; and
   a light diffusion plate controlling portion for controlling to rotate the light diffusion plate.

2. A stereoscopic image observing apparatus according to claim 1, wherein the reflecting portion comprises:
   a Fresnel lens; and
   a Fresnel concave mm or which is coated onto the Fresnel lens surface with aluminum evaporation.

3. A stereoscopic image observing apparatus according to Claim 1, further comprising:
   a camera control portion which controls the driving of a stereoscopic endoscope, performs the signal processing of a stereoscopic image which is picked up and generated by the stereoscopic endoscope, and supplies the processed signal to the first projected light illuminating portion and the second projected light illuminating portion; and
   a driving control portion which controls the driving of an image projecting panel having the reflecting portion and the diffusion portion.

* * * * *

UNITED STATES PATENT AND TRADEMARK OFFICE
CERTIFICATE OF CORRECTION

PATENT NO.        : 7,417,665 B2  
APPLICATION NO.   : 10/846969  
DATED             : August 26, 2008  
INVENTOR(S)       : Kazuo Banju et al.

Page 1 of 1

It is certified that error appears in the above-identified patent and that said Letters Patent is hereby corrected as shown below:

Column 14, Line 28, Claim 2:

"a Fresnel concave mm or which is coated onto the Fresnel"

should read

--a Fresnel concave mirror which is coated onto the Fresnel--

Signed and Sealed this

Eighteenth Day of November, 2008

JON W. DUDAS  
*Director of the United States Patent and Trademark Office*